(12) United States Patent
Burg

(10) Patent No.: US 8,256,232 B2
(45) Date of Patent: Sep. 4, 2012

(54) ULTRA-RAPID FREEZING DEVICE AND METHOD

(75) Inventor: Thomas P. Burg, Cambridge, MA (US)

(73) Assignee: Max-Planck-Gesellschaft zur Foerderung der Wissenschaften, e.V., Munich (DE)

( * ) Notice: Subject to any disclaimer, the term of this patent is extended or adjusted under 35 U.S.C. 154(b) by 958 days.

(21) Appl. No.: 12/274,653

(22) Filed: Nov. 20, 2008

(65) Prior Publication Data

US 2009/0126373 A1 May 21, 2009

Related U.S. Application Data

(60) Provisional application No. 60/989,165, filed on Nov. 20, 2007.

(51) Int. Cl.
*F25C 1/00* (2006.01)
(52) U.S. Cl. .......................................................... 62/66
(58) Field of Classification Search .................. 62/51.1, 62/66
See application file for complete search history.

(56) References Cited

U.S. PATENT DOCUMENTS

| | | | | |
|---|---|---|---|---|
| 4,707,998 | A | * | 11/1987 | Linner et al. ..................... 62/349 |
| 6,300,130 | B1 | | 10/2001 | Toner et al. |
| 6,403,376 | B1 | | 6/2002 | Toner et al. |
| 2009/0126373 | A1 | | 5/2009 | Burg |

OTHER PUBLICATIONS

Briand et al., "Thermal optimization of micro-hotplates that have a silicon island", J. Micromech. Microeng., vol. 12, pp. 971-978 (2002).
Bouwer et al., "The Application of Energy-Filtered Electroni Microscopy to Tomography of Thick, Selectively Stained Biological Samples", Methods in Cell Biology, vol. 79, pp. 643-660 (2007).
Burg et al., "Suspended microchannel resonators for biomolecular detection", Applied Physics Letters, vol. 83, No. 13, pp. 2698-2700 (2003).
Burg et al., "Weighing of biomolecules, single cells and single nanoparticles in fluid", Nature, vol. 446, pp. 1066-1069 (2007).
Dubochet, "The Physics of Rapid Cooling and Its Implications for Cryoimmobilization of Cells", Methods in Cell Biology, vol. 79, pp. 7-21 (2007).
Enoksson et al., "Fluid density sensor based on resonance vibration", Sensors and Actuators A 46-47, pp. 327-331 (1995).
Hell, "Far-Field Optical Nanoscopy", Science, vol. 316, pp. 1153-1158 (2007).

(Continued)

*Primary Examiner* — Melvin Jones
(74) *Attorney, Agent, or Firm* — Caesar, Rivise, Bernstein, Cohen & Pokotilow, Ltd.

(57) ABSTRACT

An ultra-rapid freezing device (100) adapted for cooling a sample (1), includes a substrate chip (10) being adapted for cooling the sample (1), and at least one sample carrier (20) being adapted for accommodating the sample (1) and including at least one heatable support (21), through which the at least one sample carrier (20) is attached to the substrate chip (10). Preferably, the at least one sample carrier (20) is attached to the substrate chip (10) in a suspended manner. Furthermore, a method of ultra-rapid freezing a sample (1) is described. The at least one sample carrier (20) can be switched between a heated state at which a thermal gradient is formed relative to the substrate chip (10) and a cooled state at which a thermal equilibrium is formed relative to the substrate chip (10).

36 Claims, 7 Drawing Sheets

OTHER PUBLICATIONS

Hug et al., "Generic Fabrication Technology for Transparent and Suspended Microfluidic and Nanofluidic Channels", Transducers '05 The 13th International Conference on Solid-State Sensors, Actuators and Microsystems, Seoul, Korea, Jun. 5-9, 2005, pp. 1191-1194.

Lerou et al., "Characterization of micromachined cryogenic coolers", J. Micromech. Microeng., vol. 17, pp. 1956-1960 (2007).

Marko et al., "Focused ion beam milling of vitreous water: prospects for an alternative to cryo-ultramicrotomy of frozen-hydrated biological samples", Journal of Microscopy, vol. 222, Pt. 1, pp. 42-47 (2006).

Moerner et al., "New directions in single-molecule imaging and analysis", PNAS, vol. 104, No. 31, pp. 12596-12602 (2007).

Nickell et al., "A visual approach to proteomics", Nature Reviews/Molecular Cell Biology, vol. 7, pp. 225-230 (2006).

Risco et al., "Thermal performance of quartz capillaries for vitrification", Cryobiology, vol. 55, pp. 222-229 (2007).

Van Heel et al., "Single-particle electron cryo-microscopy: towards atomic resolution", Quarterly Reviews of Biophysics, vol. 33, pp. 307-369 (2000).

Westberg et al., "A CMOS-compatible fluid density sensor", J. Micromech. Microeng., vol. 7, pp. 253-255 (1997).

* cited by examiner

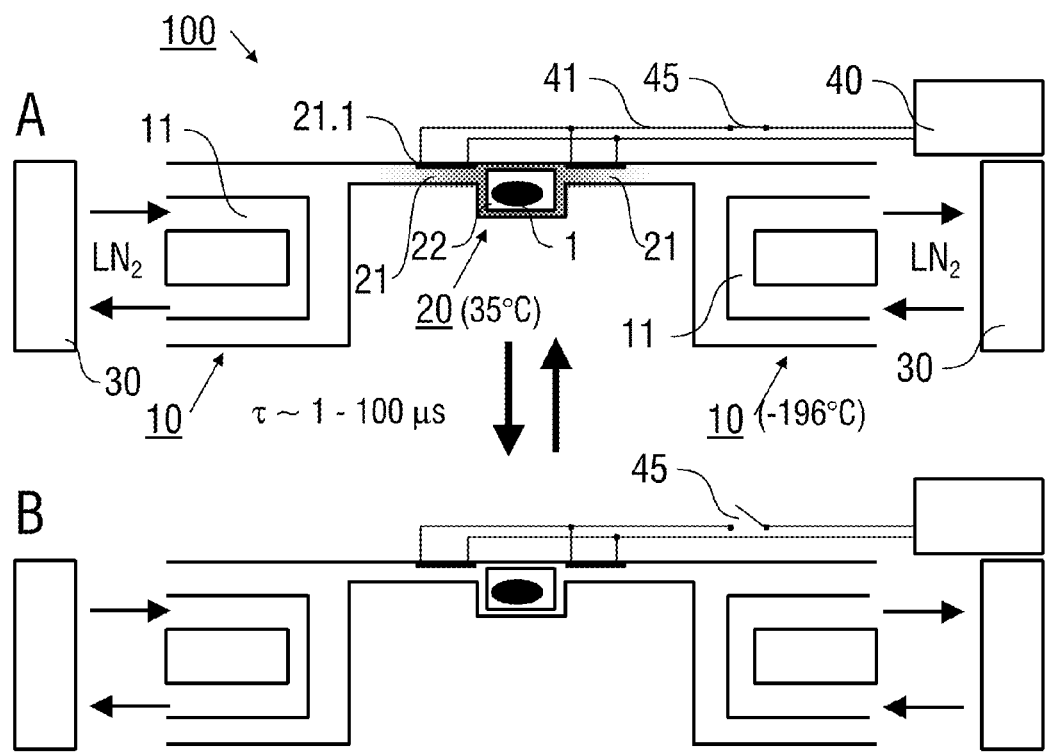
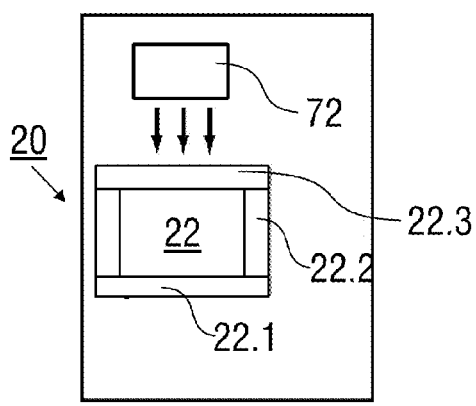

ULTRA-RAPID FREEZING DEVICE AND METHOD

CROSS-REFERENCE TO RELATED APPLICATIONS

This specification claims priority of the provisional U.S. patent application Ser. No. 60/989,165 filed on Nov. 20, 2007.

STATEMENT REGARDING FEDERALLY SPONSORED RESEARCH

This invention was made with U.S. government support under Grant #DAAD 19-03-D-0004 awarded by the Army Research Office. The U.S. government has certain rights in this invention.

SUBJECT OF THE INVENTION

The present invention relates to an ultra-rapid freezing device (flash-freezing device) for cooling a sample, in particular to an ultra-rapid freezing device being adapted for an ultra-rapid freezing of a biological sample. Furthermore, the present invention relates to a method for ultra-rapidly freezing (flash-freezing) a sample, in particular for an ultra-rapid freezing of biological samples. The invention can be applied for ultra-rapid freezing of synthetic or biological samples, in particular for investigations of biological samples, like in e.g. cryogenic imaging, or for cryofixation or cryopreservation of biological samples.

TECHNICAL BACKGROUND

Microscopy with light, electrons, and nanomechanical probes has revolutionized biology, yet at room temperature, the potential of many techniques can not be fully exploited due to thermal noise, radiation damage, or mechanical interactions with the object. Cryogenic imaging has advanced greatly in recent years, but the fixation of biological specimens for this purpose is a difficult challenge due to the need to prevent ice crystal formation upon cooling.

A conventional method of vitrifying hydrated samples (i.e. freezing while avoiding ice crystallization) is high pressure freezing, which is a laborious procedure that needs to be executed by a highly skilled operator to yield reproducible results (see J. Dubochet "The Physics of Rapid Cooling and Its Implications for Cryoimmobilization of Cells" in "Methods in Cell Biology, vol. 79: Cellular Electron Microscopy" (J. R. McIntosh), Academic Press, 2007). For biological samples, damage may also be induced by the application of high pressure (A. Leforestier et al. "Comparison of slam-freezing and high-pressure freezing effects on the DNA cholesteric liquid crystalline structure" in "Journal of Microscopy", vol. 184, 1996, p. 4-13) (~2000 bar is typical), and cells need to be removed from the environment in which they are cultured and often need to be embedded in a medium other than water for the freezing operation. Subtle alterations of cell state due to these manipulations are inherently unavoidable, and have therefore always been tacitly accepted by the community. In-situ ultra-rapid freezing eliminates disturbances (other than the rapid cooling itself) altogether, and is therefore expected to reveal a wealth of new biological insights that would otherwise remain obscured by the artifacts of sample preparation.

At atmospheric pressure, vitrification can be achieved by ultra-rapid freezing if the cooling rate is sufficiently high; the critical rate required depends on the concentration of natural or synthetic cryoprotective agents, such as, for example, salt, proteins, Dimethyl sulfoxide, or 1,2-propanediol. To prevent ice crystallization, water needs to be vitrified at cooling rates of $\sim 10^6$ K/s if no cryoprotective agent is added (R. Risco et al. "Thermal performance of qurtz capillaries for vitrification" in "Cryobiology" vol. 55, 2007, p. 222-229). However such rapid cooling currently is far beyond the limitations of conventional techniques; therefore, the requirement is usually relaxed by adding cryo-protectants, which may be toxic to the cell and can subtly alter physical structure and biochemical composition. The attractiveness of rapid cooling is then significantly diminished, since the process is not guaranteed to yield a faithful representation of the object in its natural state. Ultra-rapid cooling removes this limitation.

Large cooling rates have been obtained with a method of ultra-rapid freezing for cell cryopreservation as described in U.S. Pat. No. 6,300,130 B1 (and U.S. Pat. No. 6,403,376 B1). Biological material is placed in thermal contact with a cryogenically coolable environment, while radiation energy is applied to the biological material for melting a portion thereof. Rapid interruption of the irradiation results in a rapid cooling and vitrification of the biological material. This freezing technique has the following disadvantages. Firstly, the biological material is directly heated by the irradiation so that a radiation source has to be adapted to the absorption of the biological material resulting in a restricted application of a freezing equipment. Furthermore, damages of the biological material may occur. Thus, only a portion of cells included in the biological material may survive (about 80%). Further restrictions result from the conventional heating with a radiation beam focussed into the sample. Point-shaped vitrified sample regions can be obtained only. Also, when cells are thawed by the focused radiation source, the surrounding medium will still be frozen, preventing facile access to the sample for the purpose of exchanging media or experimental manipulations. Furthermore, a freezing front is created, which moves from a cool boundary of this region to a center thereof after switching-off the irradiation. An inhomogeneous sample structure may result even in the center of the vitrified region. Similarly, the inhomogeneous temperature distribution in the thawed state is problematic for live samples, which will be exposed to temperature gradients from the freezing point of water to approximately 40° C. over distances of the order of 10 μm.

Efforts for obtaining efficient cooling with large cooling rates have been made not only in the field of ultra-rapid freezing of biological samples but also in other technologies, like electronics, sensor techniques and chemical engineering, e.g. for switching operation conditions or adjusting reaction conditions of a chemical reaction.

OBJECTIVE OF THE INVENTION

It is the objective of the present invention to provide an improved ultra-rapid freezing device, which is capable of avoiding disadvantages of conventional cooling techniques. In particular, the ultra-rapid freezing device is to be capable of freezing a biological sample at a cooling rate allowing a sample vitrification at atmospheric pressure without using a cryo-protectant. It is another objective of the invention to provide an improved ultra-rapid freezing method avoiding disadvantages of the conventional techniques.

These objectives are solved with an ultra-rapid freezing device and an ultra-rapid freezing method of the invention.

SUMMARY OF THE INVENTION

According to a first aspect of the invention, an ultra-rapid freezing device is provided, which comprises a substrate chip and at least one sample carrier being connected with the substrate chip through one or multiple heatable supports. The substrate chip with the at least on sample carrier attached thereto is a micro-engineered device (microstructure device, e.g. microfluidic chip). The at least one sample carrier is adapted for accommodating a sample, like e.g. a biological sample. The substrate chip is arranged for cooling the at least one sample carrier and the sample accommodated therein down to a temperature below 0° C., in particular below the glass transition temperature of the biological sample. Cooling is preferably conducted at atmospheric pressure or at a reduced pressure below atmospheric pressure.

According to the invention, the at least one sample carrier is in thermal conduction contact with the substrate chip exclusively via the at least one heatable support. To this end, the at least one sample carrier preferably is attached to the substrate chip in a suspended manner. The term "suspended" means that the at least one sample carrier is mounted self-supported at the micro-engineered device. The heatable supports preferably comprise rod- or beam-shaped elements having a solid or hollow structure.

The heatable supports, which have a double function of holding, in particular suspending, the at least one sample carrier and providing the thermal contact with the substrate chip, can be heated so that there is no net heat loss from the at least one sample carrier to the substrate chip.

When the heating of the heatable supports is stopped, a thermal equilibrium between the at least one sample carrier and the substrate chip can be formed. The inventor has found that the thermal equilibrium can be obtained with an extremely short transition time in the sub-ms range (ultra-rapid freezing or flash-freezing) resulting in a high cooling rate which e.g. allows a vitrification of the biological sample. The terms "ultra-rapid freezing" or "flash-freezing" are equivalently used in particular for cooling a complete sample from room temperature to a temperature below 0° C. in less than 1 ms, in particular below 50 μs.

As a further advantage, the inventive ultra-rapid freezing device has an enlarged area of application in terms of freezing various types of samples (or generally: objects), such as synthetic or biological materials, liquids, and/or solid materials. Contrary to the above conventional technique of U.S. Pat. No. 6,300,130 B1, there is no need to adapt the ultra-rapid freezing device to the sample type to be frozen. Due to the indirect freezing via switching of the heating effect of the heatable supports, there is no restriction with regard to e.g. selecting a certain irradiation wavelength for direct heating. Furthermore, in contrast to the conventional technique of U.S. Pat. No. 6,300,130 B1, a uniform temperature distribution can be provided inside the at least one sample carrier, since the heat dissipated in each heatable support can be adjusted to precisely balance the heat lost by thermal conduction through the same support.

According to a second aspect of the invention, an ultra-rapid freezing method is provided, wherein the sample to be cooled, in particular a biological sample to be frozen, is arranged on a sample carrier, which is attached to a substrate chip through at least one heatable support. As long as the heatable supports are heated, a thermal gradient can be maintained between the sample carrier and the substrate chip, so that e.g. biological cultivation conditions or any predetermined operation conditions, like in particular room temperature, can be obtained in the sample carrier. With a stopping of the heating of the heatable supports, the thermal gradient is destroyed and the sample carrier is cooled down to a temperature provided by the substrate chip or a part thereof. Thus, the sample is transferred to a cooled condition.

Preferably, the ultra-rapid freezing method is conducted with the ultra-rapid freezing device according to the above first aspect of the invention.

With a particularly preferred application, a method is proposed to enable e.g. the culturing, stimulation, and in-situ, reversible, and repeated ultra-rapid freezing of single cells on a microfluidic chip without the need for chemical cryo-protectants. The enabling concept is in particular to suspend cells in a free-standing microfluidic channel that has a low volume and a very short thermal time constant. If the channel is connected to a cold reservoir of the substrate chip through the heated supports, cells and nutrients can be delivered while the heaters keep the fluid at room temperature. When the heaters are switched off, the channel will rapidly equilibrate with the reservoir and result in vitrification of the sample if the thermal time constant is sufficiently short (see below, FIG. 1).

About fourteen picoliter is the largest drop of water that can be vitrified directly from room temperature without the use of cryo-protectants. This is not a technological limitation, but it arises from the finite thermal conductivity of water limiting the cooling rate at the center of the drop. Similarly, a long cylinder, such as a pulled capillary, must be less than approximately twenty micron in diameter to enable vitrification of pure water. These numbers illustrate that, in principle, a wide range of bacteria, plant, and animal cells are amenable to direct cryofixation.

Among the most intriguing aspects of fixing and imaging cells at low temperature is that they can be preserved in a hydrated, near-natural state, and that cells and molecular machines may be literally 'frozen' in short, transient states—a distinct advantage over chemical fixation.

Microfabrication of the inventive ultra-rapid freezing device provides unique flexibility through lithographic patterning, a wide choice of materials with thermal conductivities spanning two decades, and possible wall thicknesses from less than one micron to more than one hundred micron. Conventional methods like, for example, the pulling of glass capillaries, are severely limited in this regard. One aspect of the proposed system where this is crucial is lithographic patterning to allow the integration with microfluidics for the controlled delivery of cells, growth media, and different chemicals to the suspended channel.

Thus, as a particular advantage, the sample carrier of the micro-engineered ultra-rapid freezing device can be provided with various shapes and dimensions. According to a first variant of the invention, the sample carrier is a channel (microfluidic channel). The channel provides a space for the sample having a longitudinal extension. Preferably, the length of the channel is essentially larger than the cross-sectional dimensions, e.g. by a factor of 100. The channel can be a closed channel being covered with a cover wall or an open channel, in which the sample is exposed.

Using a microfluidic channel as the sample carrier has the following advantages. Firstly, provision of a through-flow system is facilitated. Supply tubes can be connected with the ends of the channel for delivering and discharging the sample and/or additional liquids, like e.g. chemical reaction partners or cultivation media. Furthermore, despite small cross-sectional dimensions, a relatively large volume of the sample can be subjected to the ultra-rapid freezing at once. Furthermore, the channel provides an enclosure with an improved protection of the sample during the steps of the ultra-rapid freezing or further investigation. This enclosure would, for example, allow the entire apparatus to be placed in a vacuum to prevent condensation of atmospheric water vapor, while the sample would be shielded from the vacuum environment by means of the channel walls.

The suspended microchannel design admits a number of variations to the general inventive concept outlined. Thus, according to a second variant of the sample carrier, a platform or membrane can be provided, which is suspended to the substrate chip. In both cases, the sample carrier comprises a free-suspended plate or sheet. As a main advantage, the platform or membrane allows an ultra-rapid freezing of samples with an exposed surface. Manipulations of e.g. biological samples, in particular in a cryopreserved state are facilitated. Furthermore, using a platform or membrane can have advantages in terms of supplying the sample in a liquid state with a dispenser device.

On a platform, a layer of cells can be formed and subjected to ultra-rapid freezing. As an example, a network of nerve cells can be cultivated and stimulated with electrodes integrated into the platform. During measuring cell potentials, the ultra-rapid freezing can be performed.

According to a third variant, a hollow cavity (cup-shaped compartment) can be used as the sample carrier. This may have advantages in particular with regard to ultra-rapid freezing of small sample amounts. Preferably, the cavity has an opening for delivering the sample. Alternatively, it can be adapted for a complete enclosure of the sample.

According to preferred embodiments of the invention, the sample carrier has a wall thickness in a range below 500 μm. The wall thickness is e.g. the thickness of the bottom, side and cover walls of the channel, the thickness of the platform or membrane or the thickness of the cavity wall. Particularly preferred is a wall thickness in a range from the sub-μm range, in particular above 50 nm, like from 100 nm or 200 nm, to more than 1 μm, like e.g. 2 μm or 5 μm. The inventor has found that a sample carrier having such a wall thickness is optimized with regard to a rapid freezing process (low thermal capacity), while having a sufficient mechanical stability even during the heating and cooling steps.

According to further preferred embodiments of the invention, the sample carrier has cross-sectional dimensions in the range of 100 nm to 200 μm, in particular in the range of 500 nm to 50 μm. As a preferred example, the sample carrier has a rectangular cross-section with a width and height selected in the cited ranges.

According to a further preferred embodiment of the invention, the ultra-rapid freezing device is designed as a through-flow device. At least one, preferably two supply tubes are connected with the at least one sample carrier. As examples, the supply tubes are extensions of the microfluidic channel or tubular lines connected with the surface of the platform or membrane or with the hollow cavity. Generally, the supply tubes are thermally isolated relative to the substrate chip. In particular, the supply tubes are arranged with a distance relative to the cold reservoir of the substrate chip. Providing the through-flow system results in the advantageous capability of exposing biological samples trapped in the channel to circulating media or to time-varying concentrations of stimulating substances. Examples of methods for trapping biological samples such as cells in microfluidic channels include, but are not limited to, adhesion to the walls via special coatings (e.g. poly-lysine) or mechanical trapping at a constriction or sieve structure lithographically defined inside the channel. As a further advantage, the flow-through configuration also enables investigating increased sample amounts.

Preferably, a central section of the sample carrier, like e.g. a central region of the microfluidic channel, is thermally isolated from the supply tubes. To this end, the supply tubes preferably can be placed far enough away from the central region, thus exploiting the high thermal resistance in the axial direction for passive insulation. The thermal isolation of the central section relative to the supply tubes can also be obtained by creating gas bubbles at one or both ends of the channel. Typically, the bubbles can be formed by an injection through a side channel (e.g. via a T-junction), an electrolysis and/or a transient local heating in the micro fluidic channel.

Advantageously, the sample carrier can be adapted for combining the ultra-rapid freezing of the sample with further investigations or manipulations. Particular advantages for characterizing e.g. biological samples are obtained, if the sample carrier is adapted for at least one of an imaging of the sample, electrophysiological stimulations of the sample and measurements at the sample. Imaging the sample may comprise e.g. optical microscopic imaging with visible or ultraviolet light, fluorescence microscopy, or imaging with particle beams or electromagnetic radiation, like transmission electron microscopy, X-ray diffraction, or X-ray microscopy. As an essential advantage for biological applications, the inventive ultra-rapid freezing device allows an investigation of the functionality of cell components, e.g. by correlating optical microscopy with a subsequent investigation of the cell structure on a molecular level.

For obtaining a high cooling rate of $10^6$ K/s or even larger, the sample carrier and the heatable supports are preferably made of a material having a thermal conductivity equal to or exceeding the thermal conductivity of single crystal silicon (~150 W $m^{-1}$ $K^{-1}$). In view of the manufacturing of the ultra-rapid freezing device with the techniques of micro-engineering, the preferred material of the sample carrier and the heatable supports as well as the substrate chip is single crystal silicon. Other materials that would be suitable are copper, gold, aluminium, zinc, or various other metals, which may be deposited and patterned lithographically or electroplated into lithographically defined moulds.

Advantageously, the heatable supports can be designed for various heating techniques. Preferably, a resistive heating is provided. The heatable supports are electrically connected with a heating current source. During heating, the heating current flows through each of the heatable supports.

Preferably, the heatable supports are provided with resistive elements (resistor portions). Alternatively, a heating current can be directed through the suspended channel itself. Electrical heating has advantages in terms of integrating the heaters in optimal locations on the ultra-rapid freezing device, in particular into the channel and the heatable supports. Alternatively or additionally, a radiation heating of the heatable supports can be provided, e.g. by an irradiation with a focused laser beam. Advantageously, IR laser beams can be used for radiation heating the heatable supports.

According to a further advantageous embodiment of the invention, the heatable support may have a hollow structure guiding a cooling medium. Instead of suspending the channel by solid heated beams, the support beams themselves could be hollow and provide a path for liquid nitrogen to flow to and contact the outside wall of the suspended fluid channel. In this case, nitrogen would continuously circulate from the cold substrate through the hollow supports, which would be designed sufficiently thin so that when heated locally (electrically or through a laser), liquid nitrogen would vaporize before reaching the suspended channel. Heat loss from the suspended fluidic channel would then be greatly diminished, and the power needed to maintain the channel at room temperature would be much lower than in the solid support design.

Upon deactivating the heaters of the hollow supports, the temperature gradient would collapse rapidly, thus allowing liquid nitrogen to circulate without vaporizing and giving rise to an even faster cooling rate. This positive feedback mechanism could also be used to greatly accelerate cooling in larger microstructures (such as membranes) where passive thermal equilibration is too slow for many applications.

As a further advantage, hollow heatable supports could be used for providing at least one on-chip cryo-cooler having a local cooling effect. A plurality of cryo-coolers, e.g. one cryo-cooler in each of the heatable supports, exclusively could be used for cooling the biological sample. Alternatively, the at least one on-chip cryo-cooler could support cooling of the cold reservoir in the substrate chip.

The invention provides on-chip cooling and rapid freezing of suspended microstructures with preferred applications to the reversible and possibly repeated ultra-rapid freezing of e.g. biological samples. Aside from potentially simplifying the design of an ultra-rapid freezing device, there are numerous technologies that benefit greatly from the availability of on-chip cryo-cooling. Examples include, but are not limited to low-noise electronics, magnetic field sensors using superconducting quantum interference devices (SQUIDs), ultra-sensitive light detectors, or to temporarily slow or stop biological or chemical processes in microfluidic systems. Many of these technologies surpass the specifications of their room-temperature counterparts by several orders of magnitude. However, the technical exploitation of devices operating at low temperatures has always been hindered by the large energy consumption, physical size, and dependency on a supply of liquefied nitrogen or helium for cooling.

According to a further preferred embodiment of the invention, the ultra-rapid freezing device is adapted for switching the at least one sample carrier between a heated state and a cooled state. In the heated state, heat flow from the sample carrier to the substrate chip is compensated by the heating of the heatable supports. A thermal gradient is formed such that sample carrier and the biological sample therein has a temperature providing living conditions of the biological sample, e.g. room temperature. In the cooled state, the support heating is switched off so that the temperature of the environment, in particular the cold reservoir of the substrate chip or a cryo-cooler, is set in the sample carrier. For providing the switching operation, the ultra-rapid freezing device generally has a switching device adapted for switching the heating of the heatable supports. As an example, the switching device is provided as a switch of the heating current source or a screen shield adapted for blocking an irradiation of the heatable supports.

Preferably, the at least one sample carrier can be switched from the heated state to the cooled state with a time constant in the range of 10 μs to 1 ms. With the inventive sample carrier, a cooling rate on the order of $10^6$ K/s can be obtained. Switching from the cooled state to the heated state typically is less critical for water containing samples like biological samples. Nevertheless, rates of at least $7 \cdot 10^5$ K/s have been obtained for heating the at least one sample carrier in numerical experiments.

According to the invention, one single sample carrier can be attached to the substrate chip. This embodiment may have advantages in terms of a small size and reduced complexity of the ultra-rapid freezing device. Furthermore, the adaptation of the ultra-rapid freezing device to a measuring device, like e.g. a microscope is facilitated. Alternatively, a plurality of sample carriers can be attached to the substrate chip. This embodiment may have advantages for the simultaneous investigation of a plurality of samples.

The main application of the invention comprises cryofixation of biological samples. Advantageously, various types of biological samples can be subjected to the inventive ultra-rapid freezing. Generally, the biological sample comprises a biological material included in a fluid (including gases and liquids, in particular hydrated samples surrounded by air). The biological material may comprise one single biological cell, in particular a plant cell or an animal (or human) cell, e.g. leucocyte cells or nerve cells. Alternatively, a group of biological cells can be included in the biological sample. The cells can be separated from each other in a suspension or connected e.g. as a biological tissue. As further alternatives, at least one bacterium, at least one virus, one or more cell organelles and/or biological macromolecules can be included in the biological sample. Even synthetic objects, like vesicles including biological material can be included in the biological sample. The fluid normally comprises a solution of a nutrient or a cultivation medium, but it may also be a gas if drying the sample is desirable. Accordingly, the biological sample generally comprises a suspension or solution of the biological material in liquid, or a sample which adheres to the sample carrier and is surrounded by the fluid simultaneously supported by the carrier.

The inventive ultra-rapid freezing is characterized by an essentially improved survival rate of the biological material. According to further preferred embodiments of the invention, multiple cooling and/or heating (re-heating) steps can be provided. Advantageously, the sample can be subjected to a cultivating, stimulating, sensing, monitoring and/or processing step in the heated or cooled state of each heating/cooling cycle. In particular, another important aspect of the invention is the repeated freezing and thawing of cells. Cryopreservation is routinely used for the long-term storage of cells, and even with sub-optimal methods that do not guarantee complete vitrification, cell viability is often maintained. Although controlled and repeated freezing of a single cell at a high rate has never been possible before, many indicators exist that structure is preserved to the atomic scale, and the process of devitrification is significantly less disruptive than that of ice crystallization upon cooling (see above citation of J. Dubochet); cells therefore are very likely to continue to live and divide as normal when thawed.

According to preferred embodiments of the invention, the ultra-rapid freezing device can be equipped with at least one of the following functional devices. At least one sensor device can be provided at the sample carrier. As an advantage, sample measurements can be conducted before, during and/or after the ultra-rapid freezing. If the ultra-rapid freezing device is combined with an optical microscope, a transmission electron microscope (TEM), an electron tomography device or an X-ray diffraction or X-ray microscopy device, a characterization of the sample structure is possible on a molecular level. Finally, a destructive investigation of the sample can be provided, e.g. by a focused ion beam device (FIB) or by laser ablation, possibly combined with chemical analysis, such as mass-spectrometry.

With biological samples, the following particular procedures can be implemented. Once frozen, several imaging and spectroscopic methods can be used to gather information about the specimen. Specifically the near-zero diffusivity and reduced photobleaching of fluorescent molecules, and the possibility to use long exposure times without structural changes in the object are attractive for high-resolution imaging. Optical imaging below the diffraction limit using special schemes such as STORM, PALM, STED and several others (see review by W. E. Moerner in "PNAS" vol. 104 no. 31, 2007, p. 12596-12602 and S. W. Hell in "Science" vol. 316 no. 5828, p. 1153-1158) have become the subject of intense research over the past years. While nanometer resolution can in principle be achieved with these methods, the low signal-to-noise ratio and long averaging times (up to 12 h for a single image in PALM) present a fundamental challenge. When long exposure times are needed, cells have to be fixed, and studies of dynamic events such as cell division or the response to stimuli are not possible. Rapid freezing of single cells using the technology proposed here overcomes these limitations. Unlike chemical fixation, freezing with the inventive device or method can be reversible. Importantly, no sample preparation is required, and the time of freezing can be precisely recorded (to ~1 microsecond or better) as the sample may be observed continuously in the process.

In addition to optical imaging, electron microscopy and electron tomography may also be used to image vitrified samples. New developments in electron microscopy have enabled tomographic imaging of thick specimens (up to several microns) (see J. C. Bouwer et al. in "Methods in Cell Biology", vol. 79 ("Cellular Electron Microscopy"), J. R. McIntosh, Academic Press, 2007), and significant progress has been made in the imaging of unstained, hydrated samples (see S. Nickell et al. in "Nature Reviews" vol. 7, 2006, p. 225) with nanometer-scale resolution. These and related methods can be used directly to image vitrified cells in a suspended microchannel with thin walls (in particular on the order of 50-500 nm). Cells could then be thawed and frozen and imaged again at a later time. Alternatively, focused ion-beam (FIB) techniques can be used to generate sections of the frozen structure (see M. Marko et al. in "Journal of Microscopy" vol. 222, 2006, p. 42).

Similarly, much thinner channels (a few tens of nanometer thin fluid layer and top/bottom walls) could serve to confine highly concentrated solutions of pure proteins in a thin layer, which would yield a high-quality specimen for protein structure determination by electron cryo-microscopy. Specimen preparation currently is one of the most critical and most challenging aspects of this method (see M. v. Heel et al. in "Quarterly Reviews of Biophysics" vol. 33, 2000, p. 4, p. 307-369), and the extremely rapid freezing and geometric confinement of the suspended nanochannel device would significantly facilitate this process.

BRIEF DESCRIPTION OF THE DRAWINGS

Further details and advantages of the invention are described in the following with reference to the attached drawings, which show in:

FIG. 1: a schematic illustration of a first embodiment of the inventive ultra-rapid freezing of biological cells;

FIG. 2: a sectional view of a sample carrier channel;

PREFERRED EMBODIMENTS OF THE INVENTION

Figure 3:
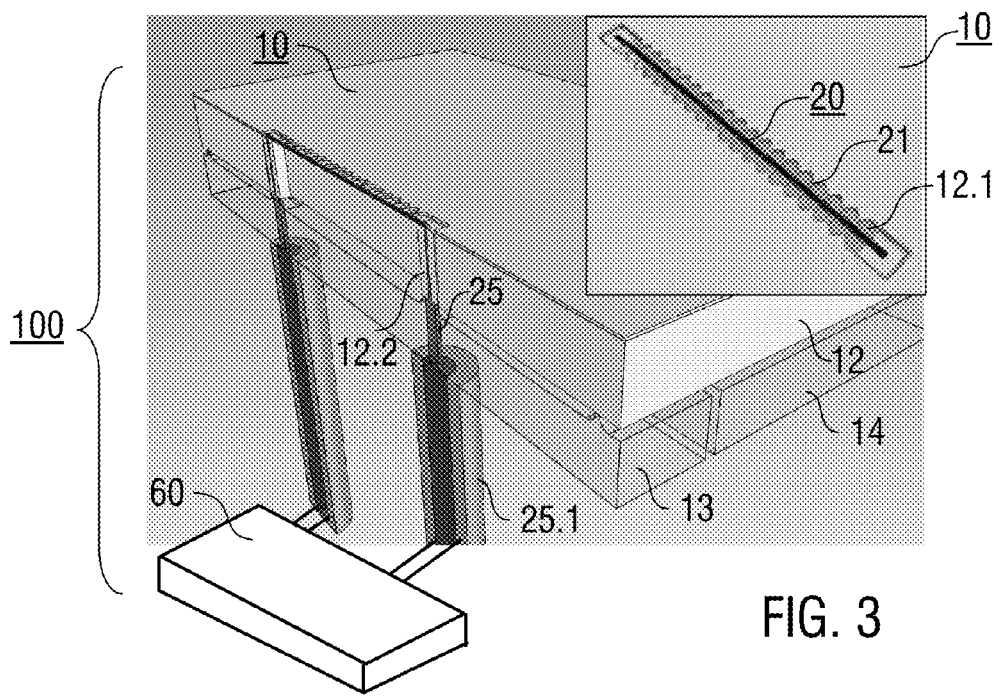
FIG. 3: a perspective, sectional view of an ultra-rapid freezing device according to the first embodiment of the invention.

Preferred embodiments of the invention are described in the following with reference to the structure of the inventive ultra-rapid freezing device and features of the inventive ultra-rapid freezing method. Furthermore, exemplary reference is made to the ultra-rapid freezing of biological samples. Details of preparing the samples for the ultra-rapid freezing, e.g. processing biological samples with microfluidic devices, and investigating samples, e.g. with optical microscopy are not described as far as these techniques are per se known from conventional techniques. The invention is not restricted to ultra-rapid freezing of biological samples but equally possible with synthetic objects, like chemical reaction assays or electronic circuits. Furthermore, reference is made in the following to ultra-rapid freezing with the cooling medium liquid nitrogen or vapor of liquid nitrogen. It is emphasized that the implementation of the invention is not restricted to the use of these cryo-media, but rather possible with other cryogenic liquids or gases, like e.g. liquid ethane. Furthermore, reference is made in the following to a preferred ultra-rapid freezing device including multiple heatable supports for suspending the sample carrier at the substrate chip. The invention is not restricted to the provision of multiple heatable supports, but rather can be implemented with one single heatable support only.

FIG. 1 illustrates a first embodiment of an ultra-rapid freezing device 100 according to the invention in a heated state (FIG. 1A) and in a cooled state (FIG. 1B). The ultra-rapid freezing device 100 comprises the substrate chip 10 (partially shown) and the sample carrier 20. The cross-sectional view of FIG. 1 shows that the sample carrier 20 comprises a thin microfluidic channel 22 which is attached to the substrate chip 10 through heated support beams 21. The substrate chip 10 includes a cold reservoir formed by cooling medium channels 11. The cooling medium channels 11 are formed in the chip body on opposite sides of the sample carrier. The cooling medium channels 11 are connected with a coolant supply source 30 (schematically illustrated). The coolant supply source 30 comprises a reservoir of liquid nitrogen being connected via conduction lines and control valves (not shown) with the cooling medium channels 11.

The channel 22 of the sample carrier 20 (see also FIG. 2) has a rectangular cross-section with a width in the range of e.g. 1 µm to 30 µm, e.g. 15 µm, and a height in the range of 40 nm to 40 µm, e.g. 20 µm. The longitudinal length of the channel 22 (see also FIG. 3) is e.g. 1 mm to 5 mm. The channel 22 defines a space for accommodating the biological sample 1, which comprises e.g. a biological cell being suspended in a cultivation medium, or attached to the channel walls.

FIG. 2 shows a cross-sectional view of channel 22 of the sample carrier 20. As an example, a watery sample is included in channel 22. A bottom wall 22.1 of channel 22 is made of $SiO_2$ with a thickness of 200 nm. Side walls 22.2 of the channel 22 are made of silicon with a thickness of about 3 µm. The cover wall 22.3 of the channel 22 is made of $SiO_2$ with a thickness of about 200 nm.

It is a particular advantage of the inventive ultra-rapid freezing device that the upper and lower cover wall of the channel 22 can be made with planarity and optical quality allowing investigations of the sample within the channel 22, e.g. with a light microscope 72 (operated e.g. in the visible and/or IR wavelength range) or an electron microscope. Furthermore, focused ion beam (FIB) investigations are possible as outlined below.

The heatable supports 21 are adapted for a resistive heating. To this end, resistor portions 21.1 are formed at the heatable supports 21, in particular in or on the surface thereof. A heating current source 40 is provided, which is adapted for supplying a heating current to the heatable supports via electrical connections 41. The electrical connections 41 are shown above a surface of the substrate chip 10 for illustrative purposes only. In practice, preferably the electrical connections 41 are integrated into the body of the substrate chip. A switching device 45 comprises an electrical switch of one of the electrical connections 41. Alternatively, the switching device 45 can be integrated into the heating current source 40.

The resistor portions 21.1 can be formed e.g. by implanting a dopant, like e.g. boron, phosphorous, or arsenic into the monocrystalline Si of the supports 21 or by depositing a metal, like e.g. Tantalum onto the supports 21. The electrical connections 41 are made of a low-resistivity material, like Aluminum, Copper, or Gold coating with a thickness in the range of 500 nm to more than 1000 nm.

When the heaters (heatable supports 21 with the resistive portions 21.1) are turned on, heat lost by conduction from the sample carrier 20 to the substrate chip 10 is compensated for by the heat generated in the heaters. In this heated state (FIG. 1A), the biological sample 1 may be supplied to the channel 22 in a liquid condition, in particular in a temperature range above a freezing temperature of the biological sample 1 and below a denaturation temperature thereof, like in the range of 0° C. to 50° C., e.g. at room temperature (20° C.). When the heaters are turned off, the channel temperature rapidly equilibrates with the substrate chip 10. With a typical time constant in the range of 10 μs to 1 ms, the temperature in the channel 22 is reduced down to the temperature of the cold reservoir, e.g. to −196° C. or lower. Contrary to conventional techniques, a freezing front is created, which moves from a center of the sample to the warm boundaries of the sample carrier resulting in a homogeneous structure over an extended portion of the frozen sample, e.g. 1 mm in length. The cooled state is schematically illustrated in FIG. 1B.

A particular advantage of the invention is given by the fact that the sample carrier is kept at the reduced temperature even if the surrounding environment, in particular above and below the sample carrier is at room temperature. Generally, there are no particular requirements with regard to the surrounding environment. However, in particular for optical investigations, e.g. for optical microscopy, or for avoiding condensed material on a device surface, it may be advantageous to provide a dry inert atmosphere or a vacuum for avoiding condensation of humidity on the outer side of the sample carrier 20.

Critical components of the inventive system, such as the fabrication and delivery of cells to suspended microchannels (see T. P. Burg et al. in "Nature" vol. 446, 2007, p. 1066), and the generation of large sustained thermal gradients on chip (see D. Briand et al. in "J. Micromech. Microeng." vol. 12, 2002, p. 971) have been previously demonstrated. The advantage now lies in cooling the substrate while consistently maintaining the suspended channel and all connecting tubes and reservoirs at room temperature. Vitrification of water preferably is made with a thermal time constant on the order of 100 μs (assuming cooling is done with liquid nitrogen). In particular suspended microchannels made of single crystal silicon are excellent conductors of heat and can provide such rapid equilibration times. However, since the thermal conductivity of the sample itself also limits the cooling rate, the inner cross section of the channel should be smaller than ~20×20 μm if the sample has a heat conductivity similar to that of water (~0.6 W m$^{-1}$ K$^{-1}$). Several technologies for fabricating suspended microchannels out of single crystal silicon (see above publication of T. P. Burg in "Nature", and P. Enoksson et al. in "Sensors and Actuators A" vol. 46-47, 1995, p. 327-331), silicon nitride (see T. P. Burg et al. in "Appl. Phys. Lett." vol. 83, 2003, p. 2698), silicon dioxide (see T. S. Hug et al., "Generic fabrication technology for transparent and suspended microfluidic and nanofluidic channels", in "13$^{th}$ Intl. Conf. on TRANSDUCERS'05", Jun. 5-9, 2005), and various dielectric layers available in CMOS processes (see D. Westberg et al., in "J. Micromech. Microeng." vol. 7, 1997, p. 253-255) exist and are well suited to cover fluid layer and wall thicknesses from a few tens of nanometers to hundreds of microns.

FIG. 3 illustrates a schematic perspective sectioned view of the ultra-rapid freezing device 100 with an enlarged image of the sample carrier 20 with the heatable supports 21 (insert of FIG. 3).

The substrate chip 10 is made of multiple components 12, 13 and 14, which fulfill cooling, thermal isolating and/or holding functions. The upper component 12 comprises a chip body made of single-crystal silicon including the cold reservoir like e.g. the cooling medium channels 11 (illustrated in FIG. 1). Component 10 includes a recess 12.1, in which the sample carrier 20 is suspended. Furthermore, the recess 12.1 houses silicon posts 12.2 accommodating supply tubes 25. Component 13 is a thermally isolated part of the chip body, which has room temperature (see below, FIG. 4). Component 14 is an additional cooled part of the chip body, which can be charged with a liquid cooling medium like component 11.

As shown in FIG. 3, the sample carrier 20 is attached to the substrate chip 10 via the heatable supports 21. The sample carrier 20 is hanging within the recess 12.1 of the chip body 10. The channel 22 is suspended through about 40 heatable supports 21 evenly distributed on both sides of the sample carrier 20. The number of heatable supports depends on the size of the sample carrier, but will typically be in the range of 1 to 500, preferably about 10 to 50. Typically, the heatable supports 21 may have the following dimensions. The length of the heatable supports 21 is selected in the range of 5 μm to 500 μm. A cross-sectional dimension of the heatable supports 21 is selected in the range of e.g. 1 μm to 100 μm. The distance between the heatable supports 21 in the longitudinal direction of the sample carrier 20 is typically in the range of 10 μm to 100 μm.

The inventive ultra-rapid freezing device 100 may be provided with a microfluidic device 60, which is schematically illustrated in FIG. 3. The microfluidic device 60 is arranged for at least one of the supply of the biological sample to the sample carrier 20, the supply of growth media (cultivation media, nutrients) to the biological sample in the sample carrier 20 and the supply of chemical substances, e.g. for stimulation purposes for inducing a differentiation of cells in the sample carrier, or—with non-biological application—for supplying chemical reactants. The microfluidic device 60 has a structure as it is known from conventional microfluidics, in particular including microchannels, reservoirs, pumps, valves and controls.

The microfluidic device 60 is connected via the supply tubes 25.1 with the room-temperature part 13 of the chip body, which connects via the silicon pillar 25 with the sample carrier 20.

Figure 4:
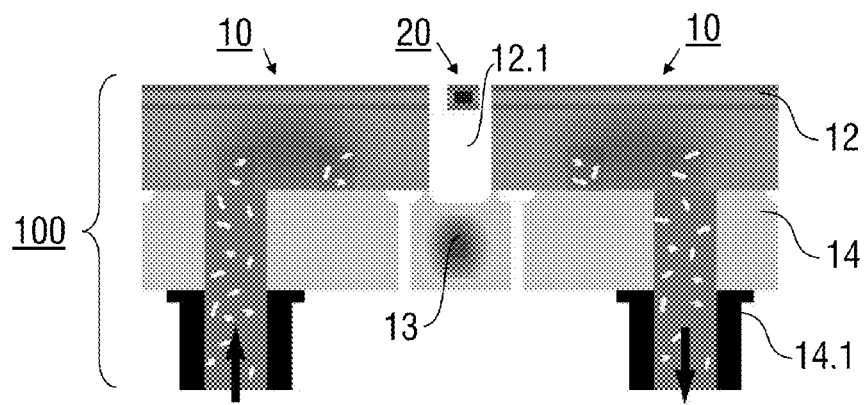
FIG. 4: a further schematic sectional view of the first embodiment of the ultra-rapid freezing device of the invention.

FIG. 4 illustrates a further schematic sectional view of the inventive ultra-rapid freezing device 100. The sample carrier 20 is arranged in the recess 12.1 of the substrate chip 10. The sample carrier 20 is attached to the substrate chip 10 as described above. Component 13 of the substrate chip 10 is made of a material that has low heat conductivity, such as glass, and component 13 is connected with the body of the substrate chip; the contact area is minimized in order to allow for reduced heat transfer between component 13, which is at room temperature, and the remainder of the substrate chip 10 (components 12 and 14), which is at lower temperature.

The embodiment of the ultra-rapid freezing device 100 according to FIG. 4 is adapted for cooling the substrate chip, with the exception of component 13, with slush of liquid nitrogen. The slush is pumped through channels 11 (see FIG. 1) via a pump device of the coolant supply device 30 (see in FIG. 1). Connection lines with the coolant supply device 30 carry a thermal insulation 14.1, which connects directly to the bottom portion 14 of the substrate chip 10.

As shown in FIG. 4, specialized packaging ensures adequate thermal insulation between the cold substrate and the fluid supply tubes. When the heaters are turned off, fluid far away from the inlets will vitrify, while water close to the ends of the suspended channel remains liquid. This spatial inhomogeneity is likely acceptable, but it may also be avoided by thermally isolating the central section of the channel through formation of bubbles on either side directly prior to ultra-rapid freezing. Suitable methods to generate small air bubbles in microfluidic channels include, for example, injection through a side channel, electrolysis, or transient local heating.

FIG. 4 illustrates one possible design for a microchip that has a substrate cooled with liquid nitrogen (or another coolant, such as, for example, slush nitrogen, or liquid ethane) and sample carrier 20 (fluid filled channel with heated support beams). The inlet and outlet of the channel are connected to fluid supplies which are always at room temperature. Mechanical rigidity and proper thermal insulation can be combined due to the unique precision of micro-engineered devices.

Figure 5:
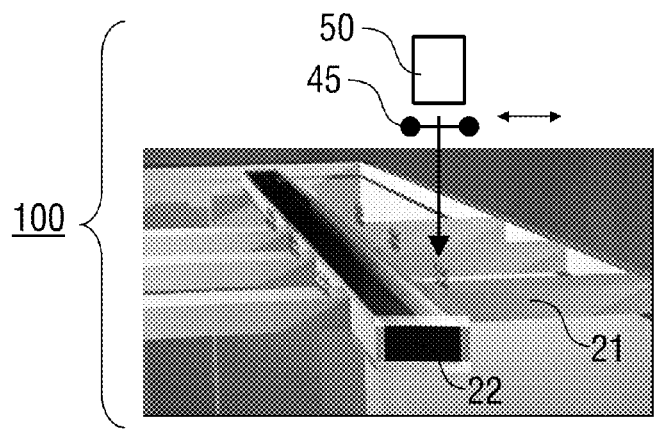
FIG. 5: a further perspective view of the sample carrier in the ultra-rapid freezing device of FIG. 3.

A modification of the ultra-rapid freezing device 100 is illustrated with a perspective, sectional view of FIG. 5. The resistive heating described above with reference to FIG. 1 can be replaced by a radiation heating as schematically shown in FIG. 5. In this case, the resistive portions 21.1 can be omitted. Radiation heating is provided with a radiation source 50, which comprises e.g. an IR laser device. IR radiation beams are directed to each of the heatable supports 21. If the radiation source 50 comprises an array of IR laser diodes, each of the heatable supports 21 can be irradiated with one of the laser diodes. Alternatively, a single laser source with an irradiation of the heatable supports 21 via a plurality of IR guiding fibers may be provided. A switching device 45 comprises in this case a movable shield adapted for blocking the irradiation. Alternatively, the switching device can be integrated into the radiation source 50.

Figure 6:
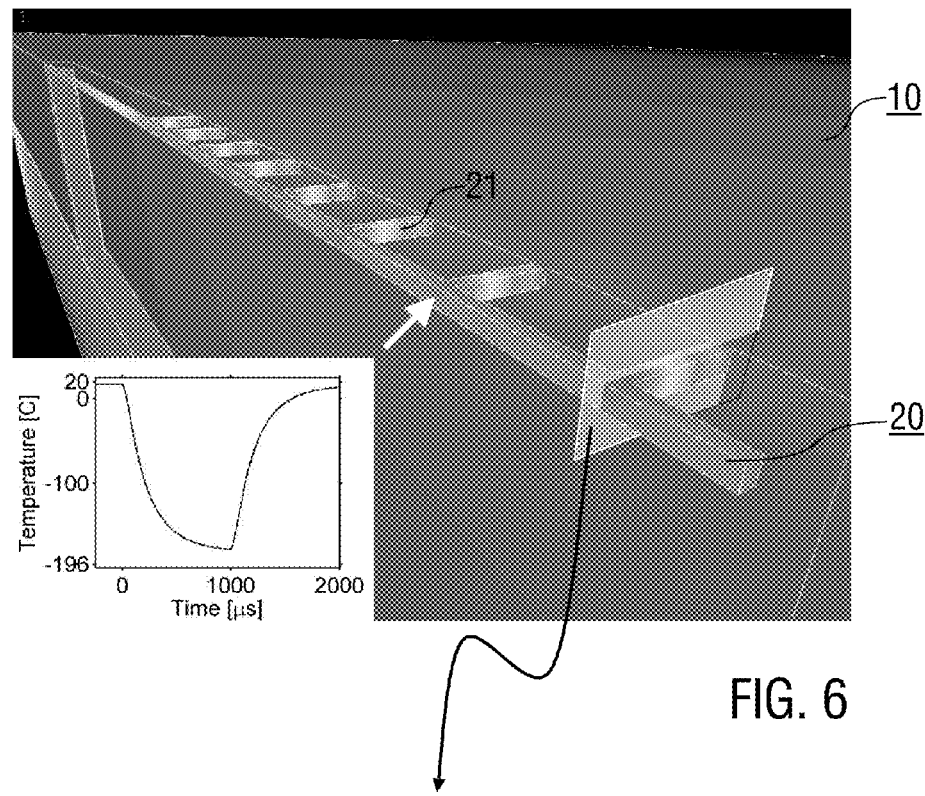
FIGS. 6 to 8: illustrations and finite-element-simulations of the thermal properties of the sample carrier in an example design of an inventive ultra-rapid freezing device.
Figure 7:
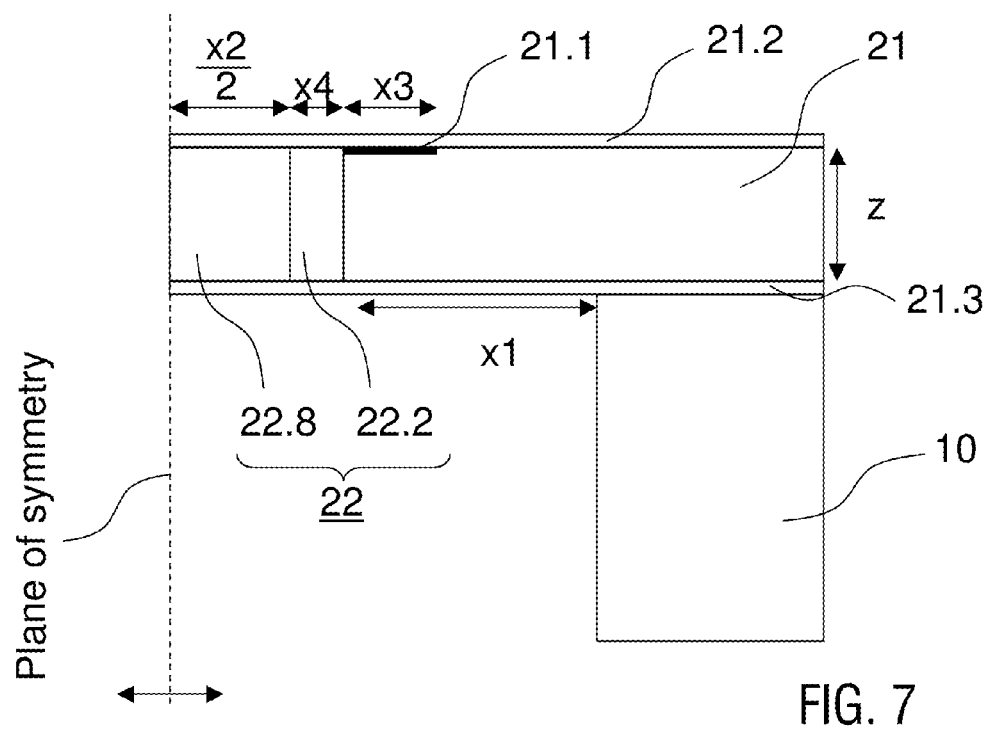
Figure 8:
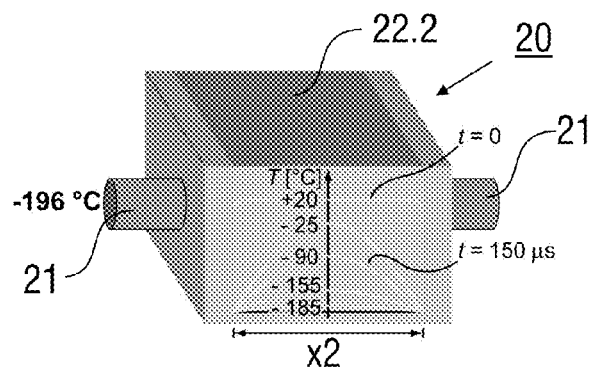

FIGS. 6 to 8 show results of theoretically simulating the heating effect of the heatable supports 21. The temperature simulation of FIG. 6 (shown with grey values) shows the distribution from −196° C. in the substrate chip 10 (grey) via the heatable supports 21 (grey gradient) to ~20° C. in the sample carrier 20 (dark grey). The insert of FIG. 6 illustrates the switching properties of the inventive ultra-rapid freezing device. The temperature of the sample carrier 20 drops below −140° C. in under 360 µs, with a maximum cooling rate of ~7·10$^5$° C./s.

The shown temperature distribution is obtained with a structure illustrated in FIG. 7 (corresponding to the frame highlighted in FIG. 6), which is made e.g. with the following parameters. Note that FIG. 6 shows one quadrant of the entire rectangular chip only, with the center of the chip coinciding with the end of the channel in the lower right corner of the figure. Correspondingly, FIG. 7 depicts the right half of the full cross-section, with the plane of symmetry indicated by the dashed line.

The heatable support 21 being made of Si between two layers 21.2 and 21.3 made of $SiO_2$ is connected with the substrate chip 10 made of Si. The thickness z of the Si portion of heatable support 21 is 10 µm while the length x1 thereof is 52 µm. The two layers of $SiO_2$ 21.2 and 21.3 are 200 nm thick. The resistive portion 21.1 has a length x3 of 20 µm and is adapted for a heating power of about 60 mW, which compensates the heat loss from the channel 22 to the cold substrate 10 when the channel is at room temperature (~20° C.) and the substrate is at −1960C. Channel 22 having the same thickness as the heatable support 21 is filled with a watery sample 22.8, which has a half-width x2/2 of 5 µm. The sample is bounded by sidewalls 22.2 made of Silicon with a width x4 of 3 µm. The finite-element simulation shown in FIG. 6 illustrates a realistic design which can be fabricated with well known microfabrication techniques.

FIG. 8 schematically illustrates a best case scenario for the development of the temperature in the sample carrier 20 with a rectangular cross-section. In contrast to the example above (FIGS. 6 and 7), here the heat capacity and finite thermal conductivity of the supports is not taken into account. The temperature profile in the watery sample 22.2 in the sample carrier 20 following instantaneous cooling of the supports 21 from 20° C. to −196° C. is calculated numerically. With a width x2 between the heatable supports 21 of 15 µm, the cooling rate is limited by the thermal conductivity of water only. The 15 µm wide silicon channel equilibrates fast enough for pure water to vitrify.

Figure 9:
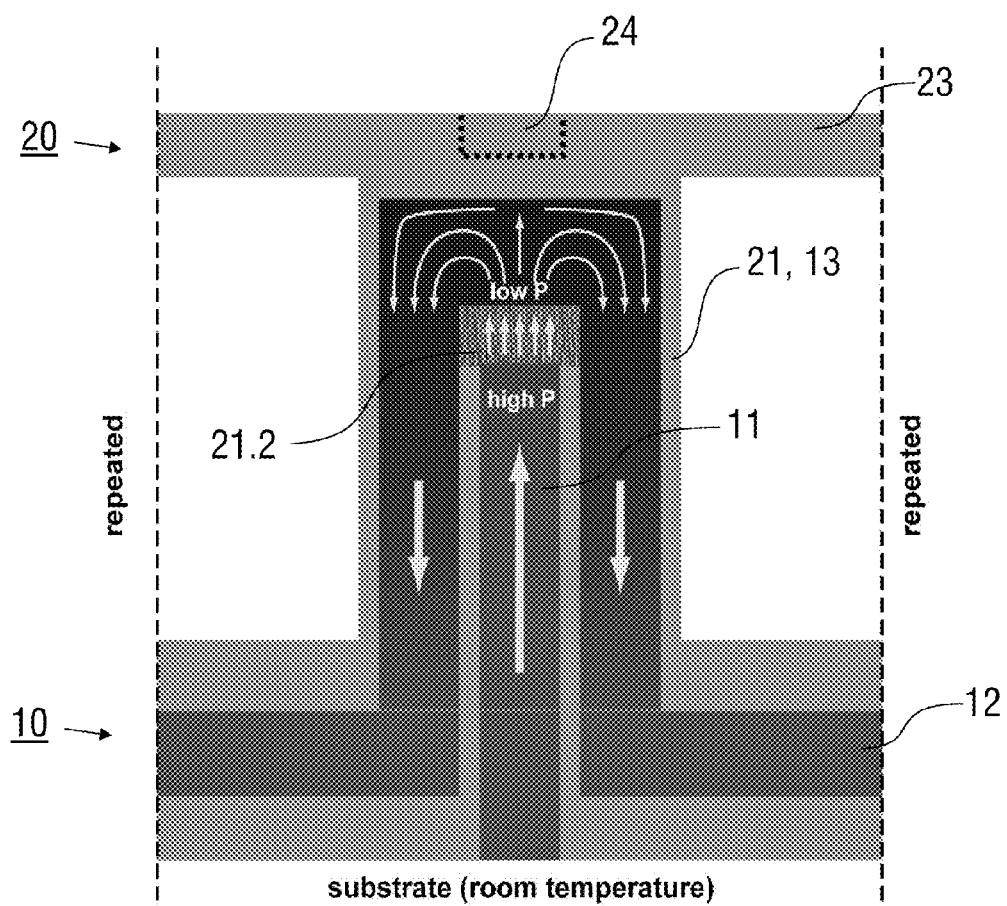
FIG. 9: a schematic sectional view of a second embodiment of the ultra-rapid freezing device according to the invention.

A second embodiment of the invention is schematically illustrated in FIG. 9 which can be considered as representing a top view or a side view of the ultra-rapid freezing device. The illustrated section of the ultra-rapid freezing device 100 shows the substrate chip 10 with cooling medium channels 11 and the sample carrier 20 comprising a platform 23 and/or a cavity 24 (partially shown). The second embodiment can be equally realized with a channel-shaped sample carrier. The sample carrier 20 is connected with the substrate chip 10 via hollow heatable supports 21 each providing a local one on-chip cryo-cooler 13. For completing the ultra-rapid freezing device 100, the section of FIG. 9 is repeated with a plurality of heatable supports 21 each suspending or supporting the sample carrier 20.

Implementing the inventive microfluidic ultra-rapid freezing device 100 can be greatly simplified by the availability of on-chip cryo-cooling. To this end, the variation of the hollow-support design is used in conjunction with a throttle structure 21.2 (nanofluidic channels or a porous plug) to enable on-chip cooling by the Joule-Thompson effect (see below, FIG. 9). On the macro-scale, this concept is well known in the form of the Linde-cycle for gas liquefaction, and attempts have been made recently to build micro-cryocoolers on the basis of this principle (see Lerou et al. "Characterization of micromachined cryogenic coolers" in "Journal of Micromech. and Microeng." vol. 17, 2007, p. 1956-1960).

However, despite the use of micromachining technology, previous implementations have not succeeded at reducing thermal losses through the counterflow heat exchanger sufficiently to enable miniaturization below the centimeter scale (at cooling powers of ~10 mW). At available cooling powers on the order of milliwatts, much smaller cold plates are used to effectively counteract heat loads due to radiation and air convection. Integrating the heat exchanger into suspended microchannels and supporting a monolithically fabricated cold plate at the end of those channels can yield more than three orders of magnitude better thermal insulation than existing techniques (based on the cross section of the heat exchanger). This provides the means for fabricating on-chip cold plates, in which the substrate can be at room temperature and only an isolated island (a few thousand to tens of thousands of square microns) is held at cryogenic temperature.

It is also possible to cascade several cooling stages to achieve successively lower temperatures, or to make arrays of coolers connecting to a single cold plate to achieve higher cooling power. One requirement for cooling by the Joule-Thompson effect is that the initial temperature of the gas is below the inversion temperature. The inversion temperature of nitrogen gas, for example, is above room temperature (649 K at 1 atm), which makes it a suitable medium to cool from room temperature to the boiling point of liquid nitrogen (77 K). Lower temperatures are attainable by using different media in subsequent stages, and by passing these media through the nitrogen-cooled stage first to enable access to a wider range of inversion temperatures.

Figure 10:
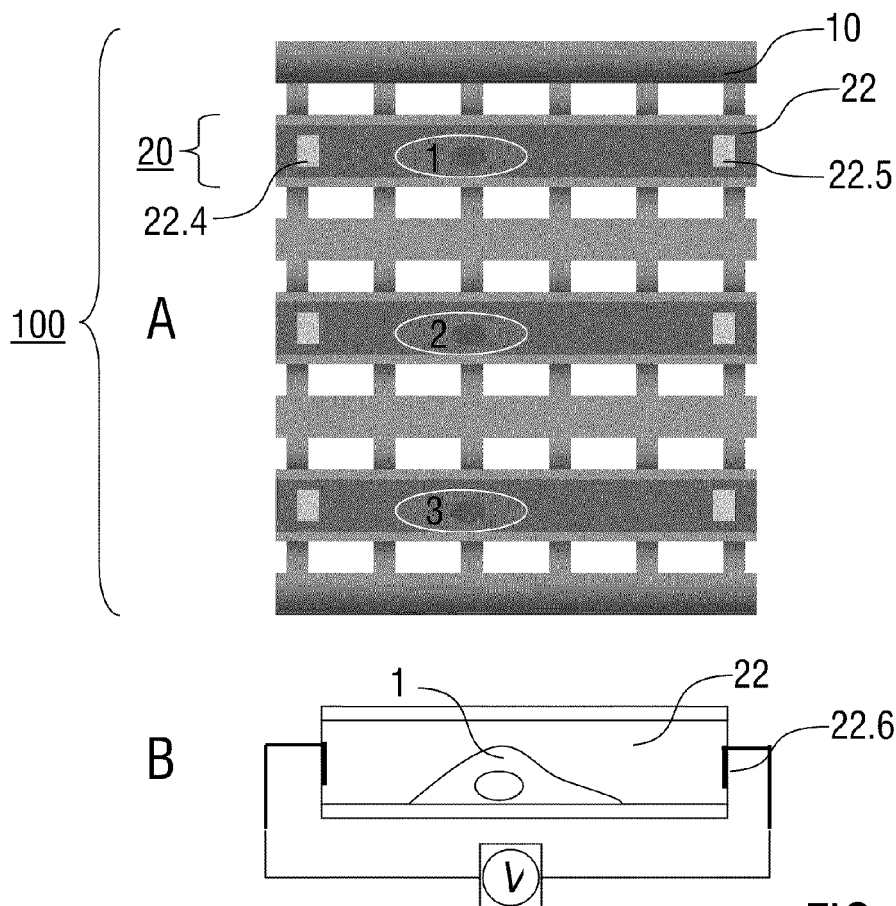
FIG. 10: a schematic top view on a third embodiment of the ultra-rapid freezing device according to the invention.
Figure 11:
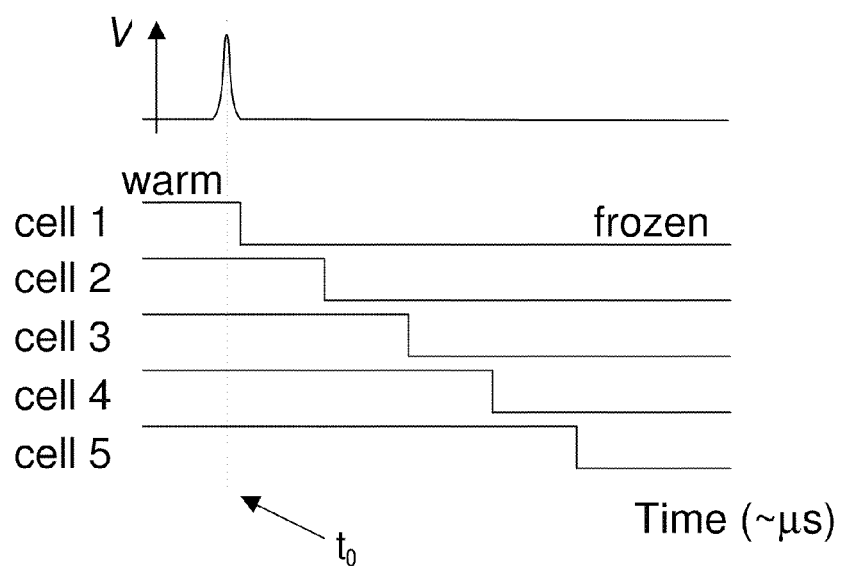
FIG. 11: an illustration of an embodiment of the ultra-rapid freezing method implemented with the embodiment of FIG. 10.

FIG. 10A illustrates a schematic top view of a third embodiment of the ultra-rapid freezing device 100 adapted for imaging of rapid transients of chemical or biochemical reactions. The ultra-rapid freezing device 100 comprises a plurality of sample carriers 20 each of which being connected with the substrate chip 10. The sample carriers 20 comprise a plurality of parallel channels 22 with inlets 22.4 and outlets 22.5. The sample carriers 20 are adapted for an electroporation of biological cells. To this end, electroporation electrodes 22.6 are integrated into the channels 22 as illustrated in the lower partial image of FIG. 10B.

Uptake and transport of fluorescent molecules after electroporation can be investigated by simultaneous imaging a plurality of cells 1, 2, 3, . . . suspended in a solution including fluorescent molecules. The cells 1, 2, 3 . . . are simultaneously subjected to a high voltage electroporation pulse at time $t_0$. Subsequently, the cells 1, 2, 3, . . . are frozen with specific delays after the electroporation time $t_0$. Imaging with optical microscopy allows a measurement of the transfer of the fluorescent molecules into the cells.

Figure 12:
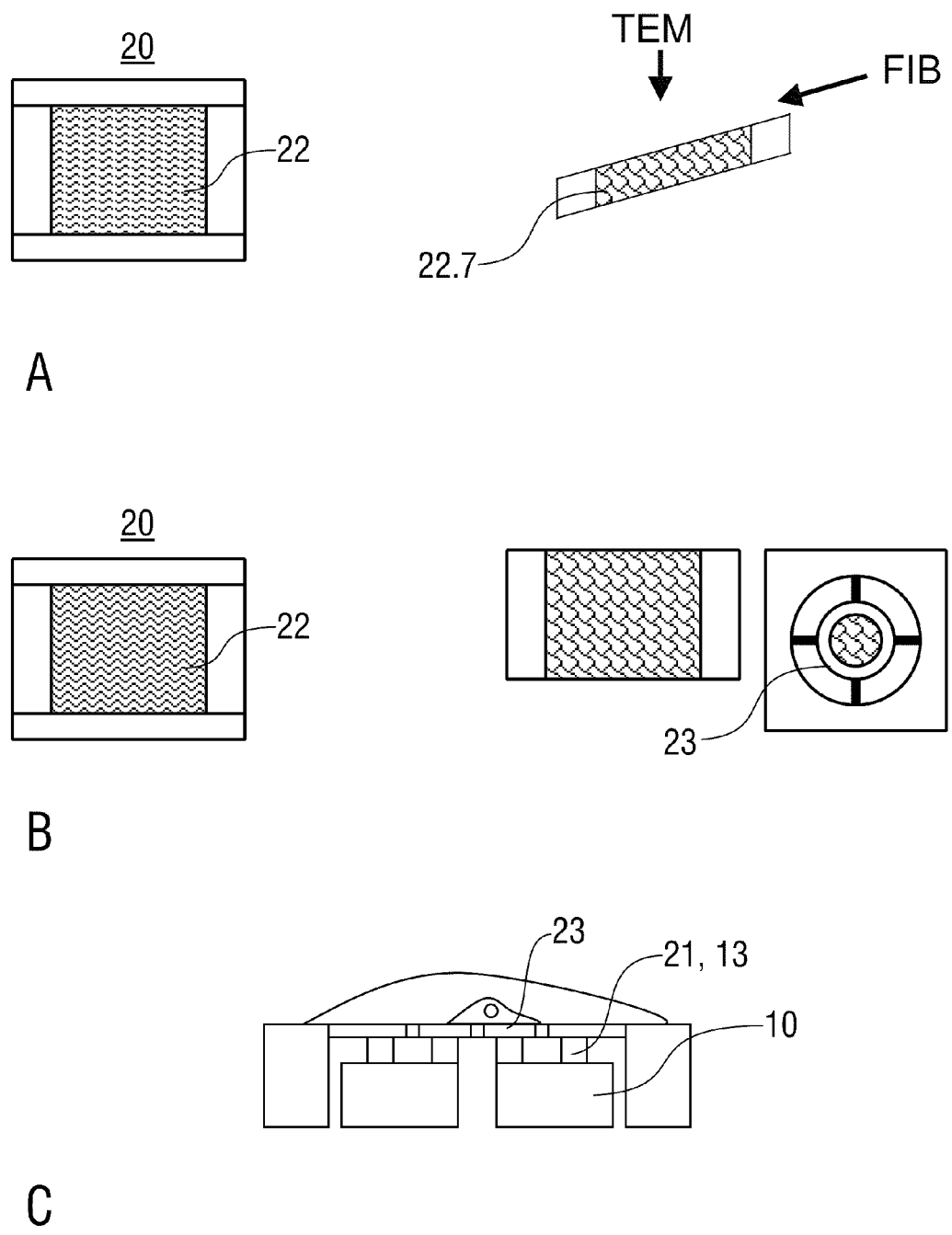
FIGS. 12 to 14: schematic illustrations of further preferred applications of the ultra-rapid freezing device according to the invention.

FIG. 12 shows further preferred applications of the inventive ultra-rapid freezing device. According to FIG. 12A, optical imaging can be combined with a (cryo-) focused ion beam (FIB) processing and TEM imaging. The channel 22 of the sample carrier 20 has a width of 15 μm and a height of 1 μm to 20 μm. The bottom and cover walls are made of $SiO_2$ (thickness about 1 μm). The sample can be monitored before, during, and after freezing with an optical microscope. Subsequently, the entire chip is transferred in a cooled condition to an FIB device. A slice 22.7 of the sample carrier 20 with a thickness of about 50 nm is produced, after which the chip is transferred into a TEM device, where it is mounted in place of a conventional TEM grid.

Figure 13:
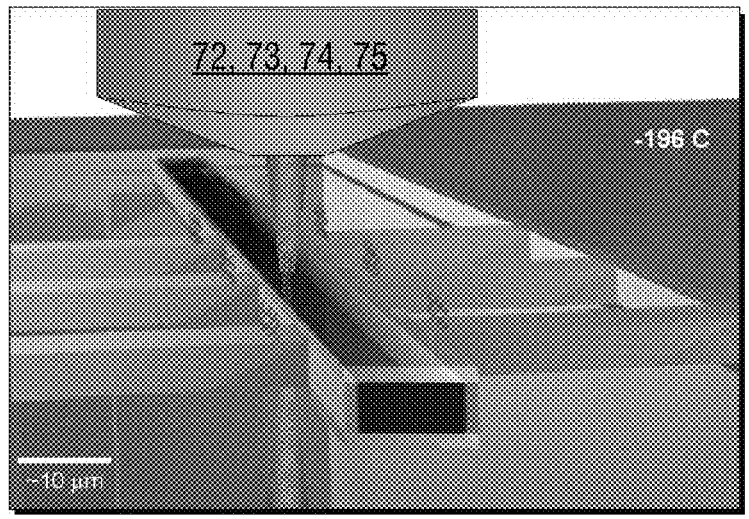

According to FIG. 12B, optical imaging can be combined with TEM imaging and/or X-ray diffraction or X-ray microscopy measurements (without FIB processing). The channel 22 with a width of 5 μm and a height of below 3 μm has bottom and cover walls made of $SiO_2$ (thickness 50 nm to 200 nm). Again, the sample can be monitored before, during, and after freezing with an optical microscope. Subsequently, the sample carrier 20 is separated from the substrate chip and transferred in a cooled condition into a TEM device or an X-ray diffraction or X-ray microscopy apparatus. FIG. 13 shows, that imaging with a microscope 72, TEM 73, an electron tomography device 74 or an X-ray diffraction or X-ray microscopy apparatus 75 or a combination thereof can be performed directly with the inventive ultra-rapid freezing device. As the sample carrier preferably is exposed for investigation, the above devices can be arranged directly adjacent to the ultra-rapid freezing device.

The right part of FIG. 12B shows a design variation adapted for open surface investigations. The sample carrier 20 comprises a circular platform 23 suspended with heatable supports 21. On the circular platform 23, a sample droplet can be formed with a curved surface depending on the surface tension thereof. Such a design would be advantageous for cryopreservation of sperm or oocytes.

FIG. 12C shows an application of the open platform embodiment of the inventive ultra-rapid freezing device. The sample carrier 20 comprises a structured platform 23 being supported by the heatable supports 21, which may simultaneously provide local cryo-cooler 13 (see FIG. 9). Optical measurements, TEM investigations, SEM investigations and the like, as well as stimulations of the sample with integrated electrodes within the platform 23 can be conducted. The sample can be formed as a thin liquid, in particular watery film made by e.g. wetting of a 3D surface structure of the platform, liquid removal by electrowetting or covering with a thin polymer cover (e.g. PDMS).

Figure 14:
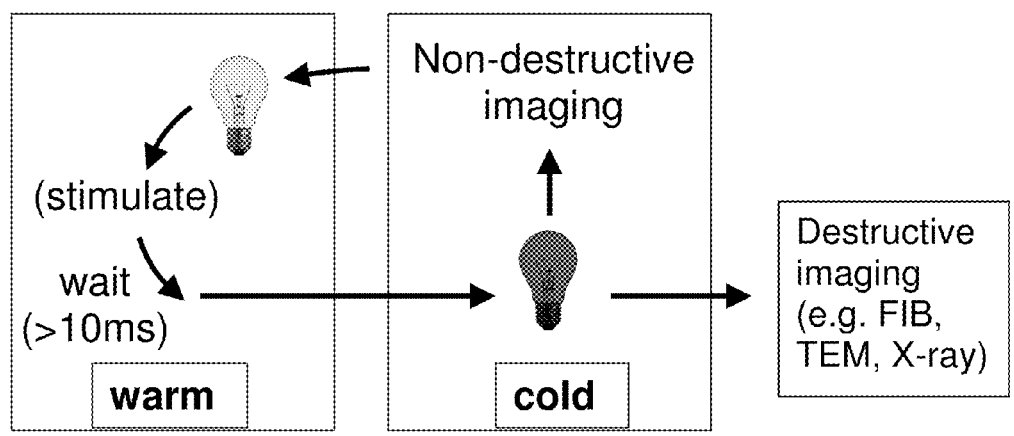

FIG. 14 illustrates another operation cycle of the inventive ultra-rapid freezing device. Non-destructive imaging can be conducted in the cooled state, while in the heated state a stimulation of the sample, or a further non-destructive imaging can be performed. This cycle can be repeated multiple times, as damaging ice crystallization during freezing and thawing is suppressed due to the high cooling and heating rates. Finally, destructive imaging can be provided for a structural analysis of the sample in the cooled state.

Figure 15:
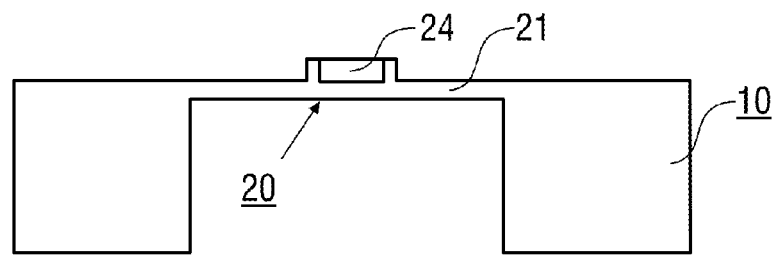
FIG. 15: a schematic sectional view of a fourth embodiment of the ultra-rapid freezing device according to the invention.

FIG. 15 schematically illustrates an embodiment of the invention wherein a synthetic object, like an electronic circuit is accommodated in the sample carrier 20. Basically, in particular with regard to the substrate chip 10, the cold reservoir and the resistive portions connected with the heat current source, the ultra-rapid freezing device is structured like the embodiment of FIG. 1. In the sample carrier 20, for example an electronic circuit or component 24, like a magnetic field sensor is accommodated. The electronic component 24 is integrated in the solid material of the sample carrier 20.

The features of the invention disclosed in the above description, the drawings and the claims can be of significance both individually as well as in combination for the realization of the invention in its various embodiments.

The invention claimed is:

1. An ultra-rapid freezing device adapted for cooling of a sample, comprising:
   a substrate chip being adapted for cooling the sample, and
   at least one sample carrier being adapted for accommodating the sample and comprising at least one heatable support, through which the at least one sample carrier is attached to the substrate chip, wherein the at least one sample carrier comprises at least one of a channel, a platform, a membrane, and a cavity.

2. The ultra-rapid freezing device according to claim 1, wherein the at least one sample carrier is attached to the substrate chip in a suspended manner.

3. The ultra-rapid freezing device according to claim 1, wherein the at least one sample carrier has a wall thickness from 50 nm to 500 μm.

4. The ultra-rapid freezing device according to claim 1, wherein the at least one sample carrier has a rectangular cross section with a width of 100 nm to 200 μm and a height of 100 nm to 200 μm.

5. The ultra-rapid freezing device according to claim 1, wherein the at least one sample carrier further comprises a through-flow device, wherein supply tubes are connected with the at least one sample carrier.

6. The ultra-rapid freezing device according to claim 5, wherein a central section of the at least one sample carrier is thermally isolated from the supply tubes.

7. The ultra-rapid freezing device according to claim 1, wherein the at least one sample carrier is adapted for at least one of an imaging of the sample and a measurement of the sample.

8. The ultra-rapid freezing device according to claim 1, wherein the at least one sample carrier and the at least one heatable support comprise a material having a thermal conductivity at least as large as a single crystal silicon thermal conductivity.

9. The ultra-rapid freezing device according to claim 1, wherein the at least one sample carrier and the at least one heatable support are made of single crystal silicon.

10. The ultra-rapid freezing device according to claim 1, wherein the at least one heatable support is adapted for at least one of resistive heating and radiation heating.

11. The ultra-rapid freezing device according to claim 10, wherein the at least one heatable support includes a resistive heater.

12. The ultra-rapid freezing device according to claim 1, wherein the at least one heatable support has a hollow structure, to which a cooling medium can be supplied.

13. The ultra-rapid freezing device according to claim 1, wherein the substrate chip includes at least one of a cold reservoir and at least one on-chip cryo-cooler.

14. The ultra-rapid freezing device according to claim 1, wherein the at least one sample carrier is switchable between a heated state at which a thermal gradient is formed relative to the substrate chip and a cooled state at which a thermal equilibrium is formed relative to the substrate chip.

15. The ultra-rapid freezing device according to claim 14, wherein the at least one sample carrier is adapted to switch between the heated state and the cooled state such that a cooling rate of at least $10^6$ K/s is obtained.

16. The ultra-rapid freezing device according to claim 1, wherein a plurality of sample carriers is attached in a suspended manner to the substrate chip.

17. The ultra-rapid freezing device according to claim 1, further comprising at least one of:
   a coolant supply device being adapted for supplying a cooling medium to the substrate chip,
   a current source being arranged for supplying a heating current to the at least one heatable support,
   a radiation source being arranged for irradiating the at least one heatable support,
   a switching device being adapted for switching the at least one sample carrier between a heated state and a cooled state,
   a microfluidic device adapted for controlled delivery of the sample, media and/or chemical substances to the at least one sample carrier,
   at least one sensor device,
   an optical microscope,
   a transmission electron microscope,
   an electron tomography device,
   an X-ray diffraction device, and
   a focused ion beam device.

18. The ultra-rapid freezing device according to claim 1, wherein:
   the sample comprises at least one of an electronic circuit, a magnetic field sensor using a SQUID device, and a light detector, and
   the sample is integrally connected with the at least one sample carrier.

19. A method of ultra-rapid freezing of a sample, comprising the steps of:
   providing the sample on a sample carrier attached to a substrate chip through at least one heatable support, wherein the substrate chip is adjusted to a cooling temperature which is below a freezing temperature of the sample,
   heating the at least one heatable support such that the sample carrier is in a heated state at which a thermal gradient is formed between the sample carrier and the substrate chip, and
   stopping the heating of the at least one heatable support such that the sample carrier is cooled into a cooled state at which a thermal equilibrium is formed relative to the substrate chip.

20. The method according to claim 19, wherein the sample in the cooled state has a temperature below 0° C.

21. The method according to claim 19, wherein the sample carrier is cooled into the cooled state at a cooling rate on the order of $10^6$ K/s.

22. The method according to claim 19, wherein the sample is a biological sample which in the cooled state is subjected to a cryofixation condition.

23. The method according to claim 19, wherein the sample in the cooled state is in a vitrified state.

24. The method according to claim 19, wherein the sample is provided to the sample carrier through a supply tube connected with the sample carrier.

25. The method according to claim 24, further comprising the step of thermally isolating a central section of the sample carrier from the supply tube through a formation of bubbles.

26. The method according to claim 25, wherein the bubbles are formed by at least one of injection, electrolysis and transient local heating.

27. The method according to claim 19, wherein the cooling of the sample carrier into the cooled state includes forming a transient freezing front within the sample, which moves from a central part of the sample carrier towards longitudinal ends thereof.

28. The method according to claim 19, wherein the substrate chip is cooled with at least one of liquid nitrogen, slush nitrogen, liquid ethane, and helium.

29. The method according to claim 19, wherein the sample includes at least one of a biological sample, an electronic circuit, a magnetic field sensor using a SQUID device, a light detector and a chemical reaction assay.

30. The method according to claim 29, wherein the biological sample includes at least one of biological cells, cell groups, cell organelles, bacteria, viruses and biological macromolecules.

31. The method according to claim 30, wherein the biological sample includes one single biological cell.

32. The method according to claim 19, comprising the further steps of:
   further heating the at least one heatable support such that the sample carrier is re-heated into in the heated state, in which the biological sample is subjected to a cultivation condition, and subjecting the biological sample to at least one of a cultivating, stimulating, sensing, monitoring and processing step.

33. The method according to claim 32, comprising the further step of cooling the sample carrier into the cooled state by stopping the heating of the at least one heatable support.

34. The method according to claim 33, wherein the heating and cooling steps are repeated for multiple reversible ultra-rapid freezing of the sample.

35. The method according to claim 19, comprising at least one of the steps of:

supplying a cooling medium to the substrate chip with a coolant supply device, supplying a heating current to the at least one heatable support with a current source, irradiating the at least one heatable support with a radiation source, controlled delivering of the biological sample, growth media and/or chemical substances to the at least one sample carrier with a microfluidic device, sensing at least one parameter of the biological sample with at least one sensor device, monitoring the biological sample in the cooled state with an optical microscope, a transmission electron microscope, an electron tomography device, or an X-ray diffraction or X-ray microscopy device, and processing the sample in the cooled state with a focused ion beam device.

36. A method of cryofixing a biological material, comprising the steps of:

providing the biological material on the sample carrier of the ultra-rapid freezing device according to claim 1, and cooling the biological material on the sample carrier to cyrofix the biological material.

* * * * *